United States Patent [19]

Nakhmanson

[11] Patent Number: 5,895,421
[45] Date of Patent: Apr. 20, 1999

[54] ARTIFICIAL HEART

[76] Inventor: Raoul S. Nakhmanson,
Waldschmidtstr. 131, 60314 Frankfurt,
Germany

[21] Appl. No.: 08/901,652

[22] Filed: Jul. 28, 1997

[30] Foreign Application Priority Data

Aug. 7, 1996 [DE] Germany ............................ 196 31 798

[51] Int. Cl.$^6$ .............................................. A61M 1/12
[52] U.S. Cl. ................................. 623/3; 417/420; 418/58;
415/900
[58] Field of Search ................................... 623/3; 418/58,
418/61.1, 68, 150, 160, 161, 209; 600/16;
415/900; 417/420

[56] References Cited

U.S. PATENT DOCUMENTS

| 348,217 | 8/1886 | Isbell . |
|---|---|---|
| 834,033 | 10/1906 | Tuttle . |
| 2,139,856 | 12/1938 | Savage . |
| 3,048,165 | 8/1962 | Norton . |
| 3,574,494 | 4/1971 | Bellmer . |
| 3,821,899 | 7/1974 | Granberg . |
| 4,173,439 | 11/1979 | Hopkins . |
| 4,652,265 | 3/1987 | McDougall . |
| 5,004,409 | 4/1991 | Nakhmanson . |

*Primary Examiner*—David H. Willse
*Attorney, Agent, or Firm*—H. Gibner Lehmann; K. Gibner Lehmann

[57] ABSTRACT

An artificial heart comprising a case with inlet and outlet openings for blood which can be implanted in human body instead of an incurable human heart and can provide the normal blood flows in both large (body) and small (lungs) blood circulations for a long period (years). It has a driving arrangement which has a driver armed with magnets and is placed outside the human body. The case is formed with cylindrical wall and two end plates and contains a movable grid consisting of twelve elongated wall elements which are disposed between said plates and which bear slidingly and sealingly on said plates, each wall element being articulately sealingly connected at its end points to at least one further wall element. The grid has nine axles; the central one is connected at least with one of the said plates, the remaining axles are free. The grid is armed with permanent magnets which cause the grid's rotation by their magnet coupling with the driving magnets of the driver. The grid has four cells and together with the end plates forms four operating chambers which alternate their volumes during rotation of grid and work as pump chambers for blood.

5 Claims, 4 Drawing Sheets

ARTIFICIAL HEART

BACKGROUND OF THE INVENTION

The invention relates to an artificial heart having at least two inlet openings and two outlet openings for blood and comprising four operating chambers of variable volume.

The field of use of the artificial heart is medicine, namely the implantation of the said heart in a human body instead of an incurable biological heart.

It is known that in industrial countries heart disease is the main reason of death. A heart transplantation is up to now the last and only radical cure. In such a case a healthy heart from a donor is used, which comes e.g. through a fatal accident. In early days there were few transplantations and the donor problem was of secondary importance. The main problems were the operation technique and suppressing the patient's natural immunity after the operation to prevent the reject reaction. Now thousands of operations are executed every year, and the donor problem is the main one. Also the reject-reaction problem can not be seen as well solved; the patient constantly depends on medicaments and is under risk of its side-effects.

The solution of donor and also largely of reject-reaction problem is the development of a mechanical artificial heart. Instead of conventional heart machines which operate in operation rooms today an implantable artificial heart must have:

1) small volume and low weight;
2) long working life (e.g. ten years);
3) low vibration;
4) a driver which is placed outside the human body and works without damaging the skin;
5) low energy consumption.

Presently available piston-, rotor-, membrane or flexible-pipe pumps can not satisfy these requirements.

The pump FIG. 1a,b which was built in accordance with U.S. Pat. No. 5,004,409 seems to be a way to fulfill the items 1)–5). It has four operating chambers 18a–d which are placed in a case 20 consisting of two end plates 2, 10 connected with a cylinder wall. The operating chambers 18a–d are formed by two parallel plates 2, 3 and a grid 4 consisting of twelve elongated wall elements which are disposed between said plates 2, 3 and which bear slidingly and sealingly on said plates, each wall element being articulately sealingly Connected at its end points (articulation points) to at least one further wall element in such a manner that said wall elements form a movable grid 4 . The grid 4 has nine joints and nine axles, respectively. The central grid's axle 7 is connected with the plate 2, the two opposite outside axles 6a,b are connected with the plate 3. The remaining six grid's axles are free. The plate 3 can be rotated around the shaft 5. During this rotation the forms and volumes of operating chambers 18a–d are changed.

In the plate 2 there are four openings 13a,b, 14a,b for blood. In FIG. 1a the plate 2 is omitted to show the grid. In spite of it the locations of openings are shown in FIG. 1a with thin lines. Connections of openings with the operating chambers are controlled by the grid's elements. In the configuration of the grid 4 shown in FIG. 1a all openings are closed, the chambers 18a,c have their maximum volume, whilst the chambers 18b,d have their minimum volume. If the plate 3 is rotated in the direction shown in FIG. 1a with the arrow, the openings 13a,b, 14a,b would be connected with the chambers 18c, 18a, 18d and 18b, respectively. The volume of the chambers 18a,c would be diminished and the volume of the chambers 18b,d would be increased. Therefore the openings 13a,b serve as outlets and the openings 14a,b serve as inlets for blood.

The case 20 would be implanted into the human body instead of an incurable biological heart in such a way that the plate 10 is placed near the skin. The ribs can be used to secure the position of the case. One outlet-inlet pair e.g. 13a, 14a can be connected to the small (lungs) blood circulation whilst another outlet-inlet pair 13b, 14b can be connected to the large (body) blood circulation.

The rotation of the plate 3 is initiated by the driver, namely by the plate 12 (FIG.1b) which is placed outside die human body near to the skin surface and is connected with the driving shaft 8. Both plates 3, 12 are equipped on their perimeters with the permanent magnets 11, 11' to create a magnet coupling.

The sealing is never perfect, and blood from the operating chambers leaks into part. 21 of the case's room outside the grid 4. Therefore this part must be washed properly with blood. The openings 15 and 16 serve for it. Through these openings part 21 can be connected (serial or parallel) to one of the blood circulations.

The disadvantages of the artificial heart FIG. 1a,b are yet a complexity and the large size and weight of its implant i.e. the case 20 and its contents.

SUMMARY OF THE INVENTION

The problem addressed by the invention is therefore to provide an artificial heart which does not have the aforementioned disadvantages.

The problem is solved with a construction which is characterized by:

two stationary plates which are arranged parallel and spaced to each other, and which together with a cylinder wall build a case, which has inlet and outlet openings for blood and is implanted in the human body instead of an incurable biological heart, twelve elongated wall elements which are disposed between said plates and which bear slidingly and sealingly on said plates, and together with said plates form four operating chambers, each wall element being articulately sealingly connected at its end points (articulation points) to at least one further wall element in such a manner that said wall elements from a movable grid having nine axles, the central axles of the said grid being connected at least with one of the said plates and at least two of the remaining axles of the said grid are equipped with permanent magnets and, the driver being placed outside the human body, which is formed as a round plate, as a bar, or as a grid being similar to the grid contained in the case, and which is equipped at least with two magnets.

DESCRIPTION OF THE DRAWINGS

The artificial heart according to the invention will be explained in detail hereinafter with the aid of the drawings, wherein:

FIG. 1b is a side vice, of the device shown in FIG. 1a.

FIG. 2b is a side view of the embodiment shown in FIG. 2a;

3

Figure 3A:
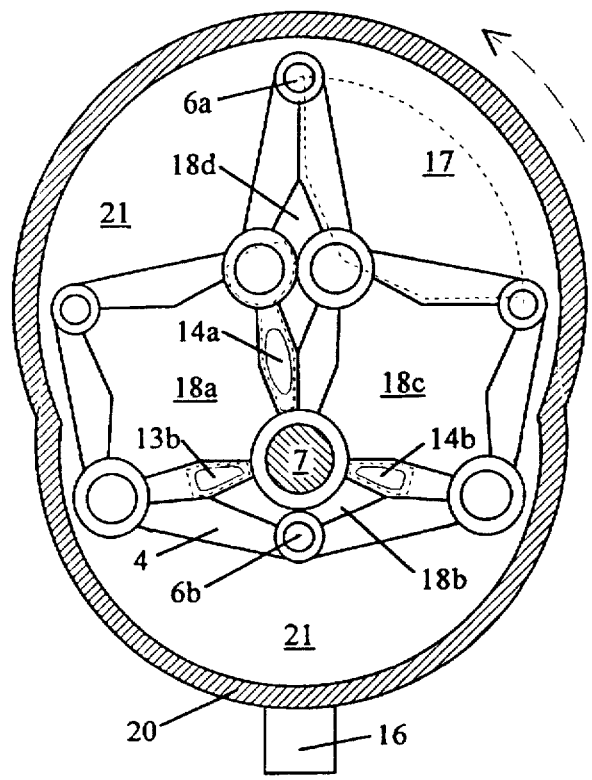
Figure 3B:
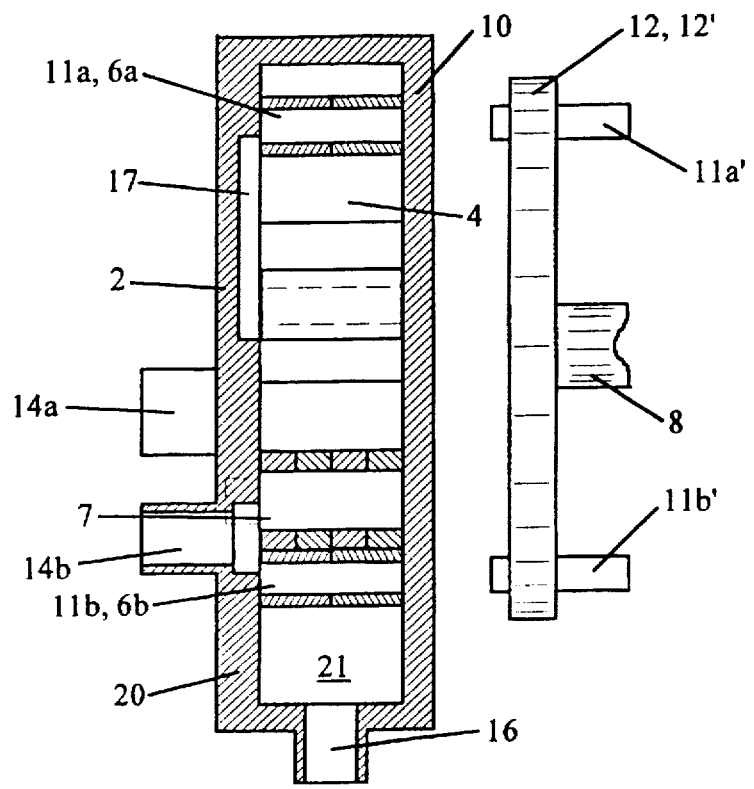
Figure 4:
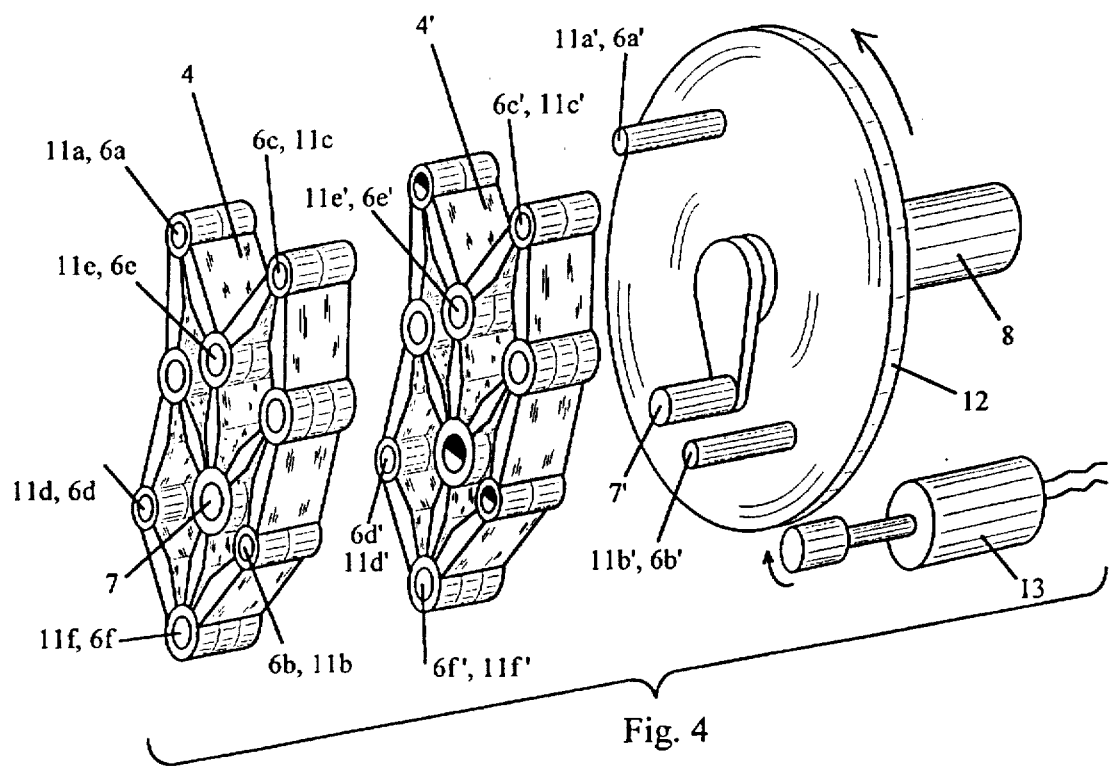
Figure 5:
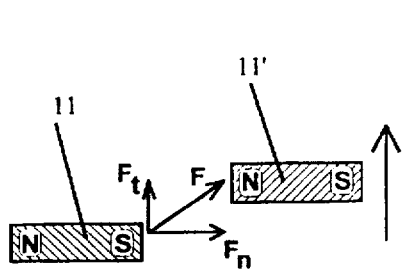
Figure 6A:
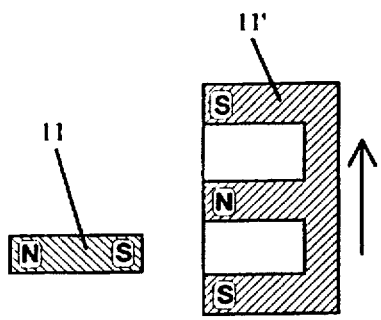
Figure 6B:
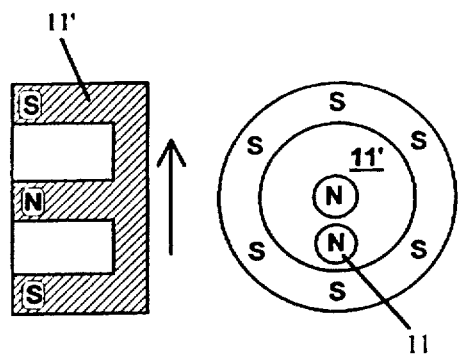

FIG. 3a shows a plan view of the artificial heart according to a further embodiment;

FIG. 3b is a side view of the embodiment shown in FIG. 3a;

FIG. 4 shows an explosion view of a further embodiment of the driving arrangement;

FIG. 5 shows an interaction between the driving and driven magnets;

FIG. 6a shows a ether embodiment of the driving magnet;

FIG. 6b is a plan view of the embodiment shown in FIG. 6a.

Figure 1A:
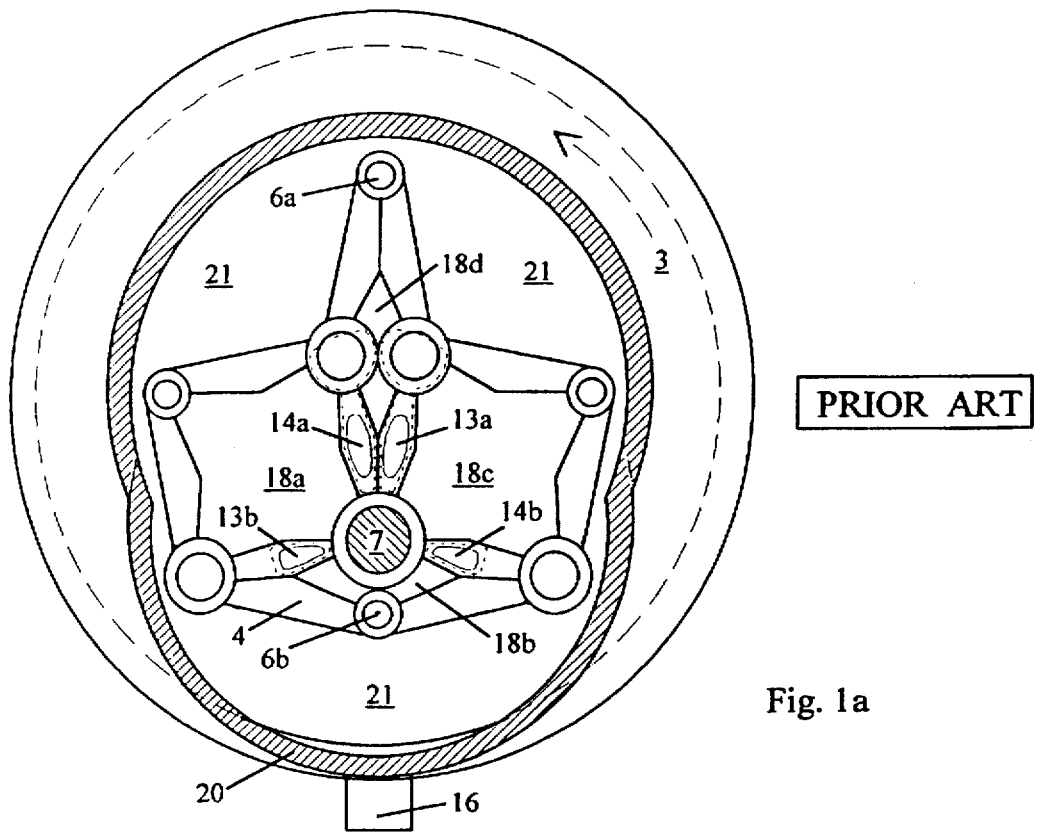
FIG. 1a shows a Plan view of an artificial heart constructed in accordance with the device described in U.S. Pat. No. 5,004,409.
Figure 1B:
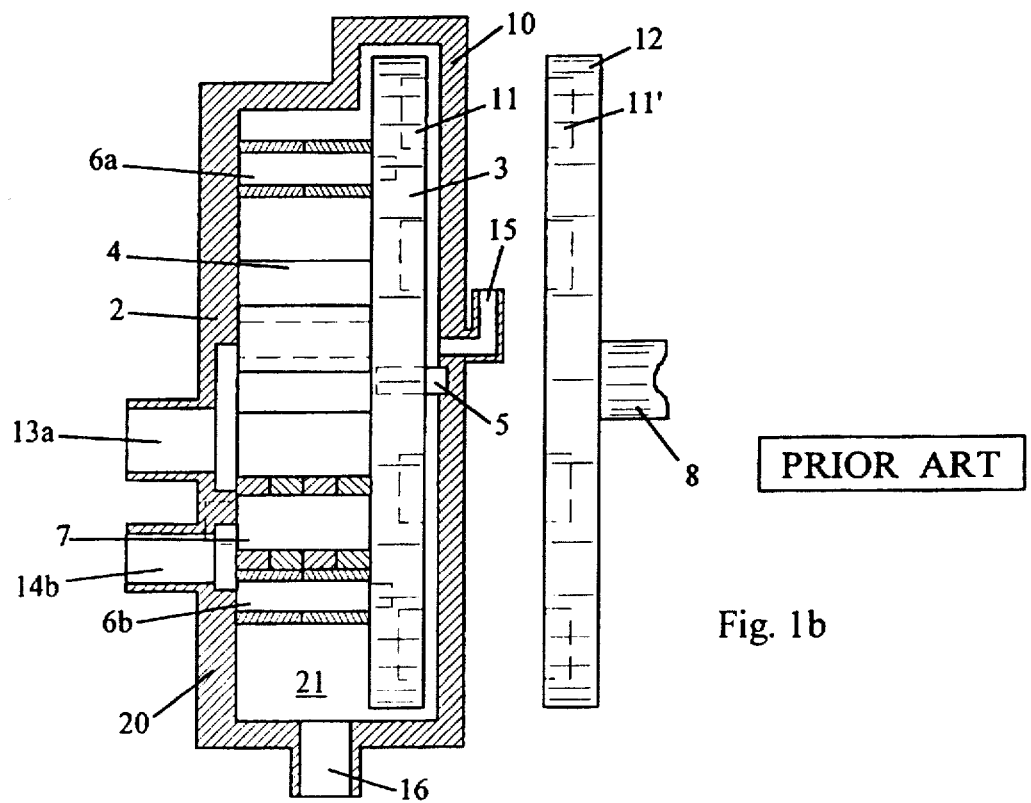
Figure 2A:
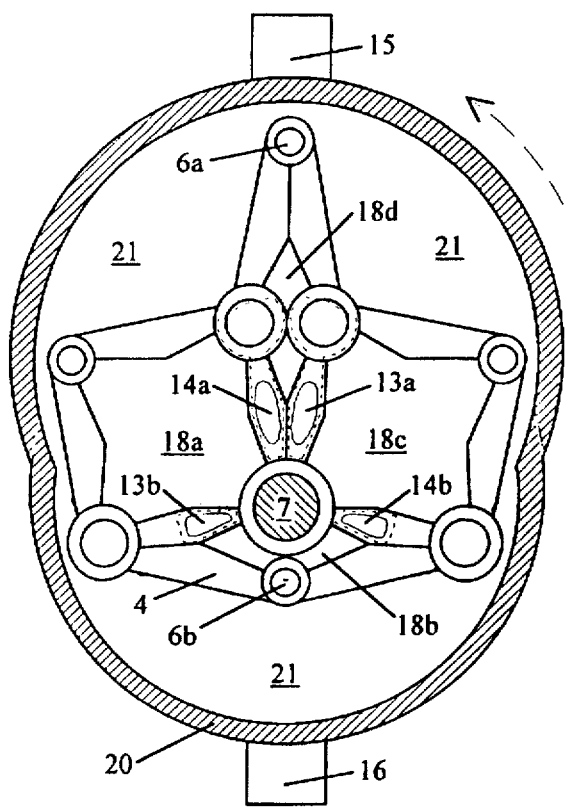
FIG. 2a shows a plan view of the artificial heart according to one embodiment of the invention.

FIGS. 2a,b show a particular embodiment of the invention. As compared with FIG. 1a,b there is no rotating plate 3 and tile grid 4 is moving directly between the plates 2 and 10. Instead of magnets 11 in the plate 3 of FIG. 1b there are magnets 11a,b in the joints/axles 6a,b (the said magnets can serve as axles 6a,b by themselves). The positions of said magnets are controlled by the corresponding driving magnets 11a',b', which are fixed in the plate 12 connected with the driving shaft 8. Instead of the plate 12 the bar 12' can be used also. If the plate 12 rotates the grid 4 follows it in the same manner as in the construction of FIGS. 1a,b. i.e. the construction FIGS. 2a,b works as an artificial heart in the same manner as the construction FIGS. 1a,b. But the implant of the construction FIGS. 2a,b (i.e. the case 20 and its contents) is essentially simple, smaller and lighter as compared with the implant shown in FIGS. 1a,b which is an important advantage.

An additional advantage of the artificial heart of FIGS. 2a,b is the possibility to fix the central axle 7 of the grid not only to the plate 2 but also to the plate 10. This makes the construction more stable and permits case 20 to have thinner walls.

The construction FIGS. 2a,b as well as the construction FIGS. 1a,b has six openings 13a,b, 14a,b, 15 and 16. As it was mentioned above the openings 15 and 16 can be connected serial or parallel to one of the blood circulations i.e. to the outlet-inlet pair 13a–14a or to the pair 13b–14b. Such a connection can be made inside the case thus reducing the number of openings to four. The correspondent embodiment of the construction with serial connection to the pair 13a–14a is shown in FIGS. 3a,b. The openings 13a and 15 are eliminated. Instead of them in the plate 2 there is the cavity 17. A similar cavity can be made in the plate 10 too. Then the grid 4 is rotated in the direction shown in FIG. 3a with the arrow, and the chamber 18c would be connected with the said cavity which in this turn is always connected with the part 21 of the cases room situated outside the grid 4. The volume of the chamber 18c would be diminished and the blood flows in the part 21 of the cases room and further to the outlet 16.

To improve the magnet coupling it is possible to equip with magnets not only the axles 6a, 6b, but also other parts of the grid 4. Because the said parts do not move as simple as the axles 6a,b, the driving plate 12 can not be simply equipped with the corresponding driving magnets. The solution is shown in FIG. 4. The plate 12 is completed here with the grid 4' which is similar to the grid 4. During rotation of the plate 12 the grids 4, 4' move identically, and therefore two arbitrary but corresponding points of the said grids can be equipped with magnets. As an example in FIG. 4 there are magnets 11a–f, 11a'–f' in the axles 6a–f, 6a'–f', respectively. The plate 12 is rotated by means of the electric motor 13 around the shaft 8, which shaft does not rotate but keeps the axle 7' opposite to the axle 7.

If the plate 12 rotates uniformly the axles 6a,b and, respectively, the axles 6a',b' rotate uniformly also. But the

Figure 2B:
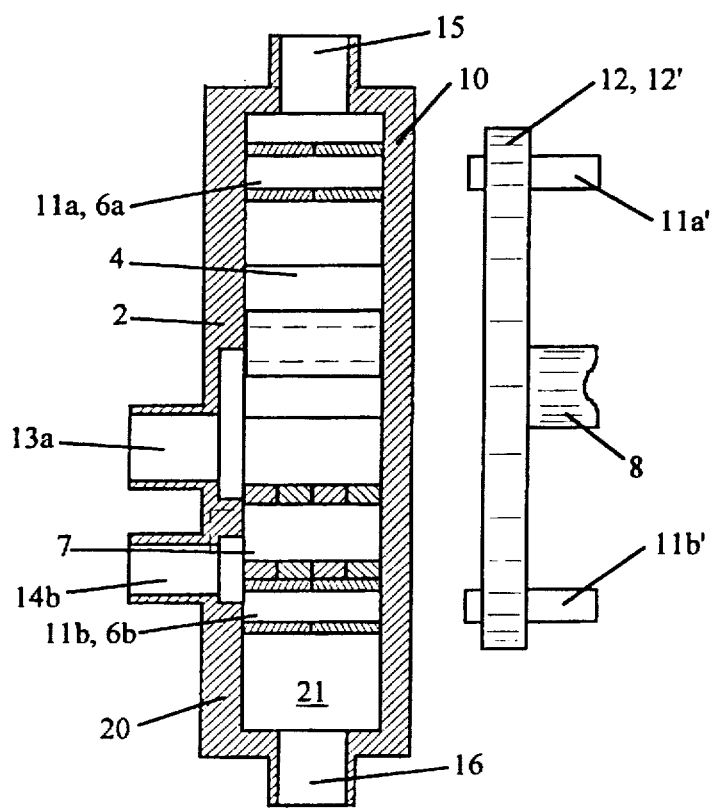

4 axles 6c',d' and, respectively, the axles 6c,d rotate nonuniformly. As a consequence the evolution of the chambers 18a,c differs from the evolution of the chambers 18b,d. In other words the odd and the even beats of the pulse produced by the artificial heart of FIG. 4 (and of FIGS. 1–3 also) are different, and this could be seen as a disadvantage. To avoid this e.g. the plate FIG. 4) can be made with an elliptical perimeter.

FIG. 5 shows the attractive force F which acts on the driven magnet 11 from the driving magnet 11' in the case both magnets are rods with north N and south S poles on their ends. The said force can be divided into two components, namely, in the tangential force $F_t$ and in the normal force $F_n$. The first one drives the magnet 11 and is useful. The second one increases the friction between the grid 4 and the plate 10 and is harmful.

FIGS. 6a,b show the further embodiment of the driving magnet 11', which has the north pole N in its center and the south pole S in its periphery. The repulsive force, which acts on the south pole of the driven magnet 11 from the south pole of the driving magnet 11', can also be divided in tangential and normal components. The said tangential component adds to the tangential component $F_t$ shown in FIG. 5 and the said normal component subtracts from the normal component $F_n$ shown in FIG. 5. Therefore both these components improve the quality of magnet coupling.

LIST OF FIGURES' REFERENCES 2 end plate
3 rotatable plate
4 movable driven grid
4' movable driving grid (also "driver")
5 shaft
6a–f axles (also "joints") of the grid 4
6a'–f' axles (also "joints") of the grid 4'
7 central axle of the grid 4
7' central axle of the grid 4'
8 shaft
10 end plate
11a–f driven magnets
11a'–f' driving magnets
12 rotatable driving plate (also "driver")
12' rotatable driving bar (also "driver")
13 electric motor
13a,b outlet openings
14a,b inlet openings
15 inlet/outlet opening
16 outlet/indet opening
17 cavity
18a–d operating chambers
20 case
21 part of case's room outside the grid 4

What is claimed is:

1. An artificial heart comprising four operating chambers with variable volume which are disposed in a case having at least one inlet opening and at least one outlet opening for blood which is adapted to be implanted in a human body and built through two end plates connected with a cylindrical wall, and a movable grid within the said case, which consists of twelve elongated wall elements, which bear slidingly and sealingly on one of said two end plates, each elongated wall element being articulately sealingly connected at its end points to at least one further of said elongated wall elements, and a driver which is adapted to be placed outside the human body and is equipped with permanent magnets, characterized in that the said elongated wall elements bear slidingly and sealingly on a second one of said two end plates too, to build the operating chambers, and the said movable grid is equipped with permanent magnets to cooperate with the permanent magnets of the said driver.

2. An artificial heart according to claim 1, characterized in that the driver is a rotating plate which is equipped with said driver magnets.

3. An artificial heart according to claim 1, characterized in that the driver is a movable grid which is similar to the grid contained in the case and is equipped with said driver magnets.

4. An artificial heart according to claim 1, characterized in that at least in one of the end plates of the case there is a cavity which in corresponding phases of rotation communicates with at least one of the operating chambers.

5. An artificial heart, comprising in combination:

a) a casing having substantially parallel, opposite coextensive walls, and having a side wall joining said opposite, coextensive walls, b) said walls having blood inlet and blood outlet openings, c) an articulated grid disposed within said casing and adapted to move therein, said grid comprising a multiplicity of articulated wall elements which are joined to produce a multiplicity of variable-volume pump chambers in said casing, some of said chambers being selectively in communication with either an inlet opening or an outlet opening, d) said wall elements having opposite end portions which slidingly and directly engage, respectively, said opposite, coextensive walls as said grid is moved within the casing, whereby the spacing between the opposite coextensive walls can be kept to a minimum, e) said grid having a magnet carried at a joint between one pair of said articulated wall elements, and f) rotating magnetic drive means disposed exteriorly of said casing, magnetically coupled with the magnet of said grid through one of the parallel coextensive walls, thereby to drive the grid transversely in the casing and vary the volume of the pump chambers, forcing blood to flow between the inlet and outlet openings of the casing.

* * * * *